USOO5360008A

United States Patent [19]
Campbell, Jr.

[11] Patent Number: 5,360,008
[45] Date of Patent: Nov. 1, 1994

[54] RESPIRATORY AND CARDIAC MONITOR

[76] Inventor: William G. Campbell, Jr., 2019 Orangeview La., Orange, Calif. 92667

[21] Appl. No.: 977,913

[22] Filed: Nov. 18, 1992

[51] Int. Cl.⁵ .............................................. A61B 5/04
[52] U.S. Cl. ...................................... 128/671; 128/902
[58] Field of Search ............... 128/903, 904, 902, 700, 128/671

[56] References Cited

U.S. PATENT DOCUMENTS

| | | | |
|---|---|---|---|
| 3,587,562 | 6/1971 | Williams | 128/902 |
| 3,638,642 | 2/1972 | Heflin, Sr. | 128/700 |
| 4,475,558 | 10/1984 | Brock | 128/716 |
| 4,889,131 | 12/1989 | Salem et al. | 128/700 |
| 5,168,874 | 12/1992 | Segalowitz | 128/903 |

*Primary Examiner*—William E. Kamm
*Assistant Examiner*—Scott M. Getzow
*Attorney, Agent, or Firm*—Klein & Szekeres

[57] ABSTRACT

A respiratory monitor (apnea detector) utilizes the discovery that the magnetic permeability of a person's body varies with the respiratory and cardiac cycles. The respiratory and optionally cardiac monitor of the invention includes an oscillator circuit which produces a signal, and a transmitter placed in close proximity of the body of the person (patient) whose respiratory cycle is to be monitored. The transmitter directs and transmits the signal originally generated in the oscillator circuit toward the trunk of the patient. A receiver-transducer is located also in close proximity of the trunk of the patient, and receives the electromagnetic signals which are modulated due to the varying permeability of the body caused by the respiratory and cardiac cycles. A signal generated in the receiver-transducer is indicative of the respiratory and cardiac cycles and is amplified and inputted into a detector circuit where the carrier frequency of the transmitter is extinguished, or otherwise separated from the modulation which is the result of the varying permeability of the body.

40 Claims, 6 Drawing Sheets

RESPIRATORY AND CARDIAC MONITOR

BACKGROUND OF THE INVENTION

1. Field of the Invention

The present invention is directed to a respiratory and cardiac monitor for humans and other mammals. More specifically, the present invention is directed to a respiratory and cardiac monitor which takes advantage of the discovery that the electromagnetic permeability of the human body varies with the above-noted body functions.

2. Brief Description of the Prior Art

Respiratory monitors (apnea detectors) of the prior art operate on the principle that impedance of the human body (primarily of the trunk) changes during the respiratory cycle. A disadvantage of these prior art apnea detectors is that one or more electrodes of the monitor are attached to the skin. As is well known in the art, attached electrodes are less than perfectly tolerated by the human body, and can cause skin irritation, rash, eczema, and in some instances even skin ulcers. Dressing and undressing of patients who have electrodes attached to the skin can also be a problem.

Another serious disadvantage of apnea detectors which operate on the principle of detecting varying impedance of the human body is that their circuitry is highly susceptible to noise, particularly noise represented by high frequency electromagnetic and electrostatic radiation. Accordingly, there exists in the prior art a need for a respiratory monitor/apnea detector which does not require the use of electrodes and is significantly less susceptible to noise. The present invention provides such a respiratory monitor/apnea detector.

SUMMARY OF THE INVENTION

It is an object of the present invention to provide a respiratory monitor/apnea detector which is does not require electrodes to be attached to the skin and is otherwise non-invasive to a patient's body.

It is another object of the present invention to provide a respiratory monitor/apnea detector which can also be adapted to function as a cardiac monitor, without the use of electrodes.

The foregoing and other objects and advantages are attained by a respiratory monitor (apnea detector) which utilizes the discovery that the magnetic permeability of a person's trunk varies with the respiratory and cardiac cycles. The magnetic permeability of the limbs also varies with the cardiac cycle. Accordingly, the respiratory (and optionally cardiac) monitor of the present invention includes an oscillator circuit which produces a signal and a transmit transducer placed in close proximity of the body of the person (patient) whose respiratory cycle is to be monitored. The transmit transducer directs and transmits the signal originally generated in the oscillator circuit toward the trunk of the patient. A receiver-transducer is located also in close proximity of the trunk of the patient, and receives the electromagnetic signals which are modulated due to the varying permeability of the body caused by the respiratory and cardiac cycles. A signal generated by the receiver-transducer which is indicative of the respiratory and cardiac cycles is amplified as necessary and is inputted into a detector circuit where the carrier frequency of the transmitter is extinguished, or otherwise separated from the modulation which is the result of the varying permeability of the body. A signal generated as the output of the detector circuit is separated into respective components due to modulation by the respiratory cycle and the cardiac cycle, and the separated signals are displayed in a visual display. The displayed or displayable signals can also be used to trigger a warning signal in the event respiration (or cardiac activity) stops for a predetermined period of time. As still other alternatives, the signals which are respectively indicative of the respiratory and cardiac cycles can be inputted into a computer (microprocessor) where they can be utilized in various programs for various purposes.

The features of the present invention can be best understood together with further objects and advantages by reference to the following description, taken in connection with the accompanying drawings, wherein like numerals indicate like parts.

DESCRIPTION OF THE PREFERRED EMBODIMENTS

The following specification taken in conjunction with the drawings sets forth the preferred embodiments of the present invention. The embodiments of the invention disclosed herein are the best modes contemplated by the inventor for carrying out his invention, although it should be understood that various modifications can be accomplished within the parameters of the present invention.

It has been discovered in accordance with the present invention that the electromagnetic permeability of the trunk portion of the human body changes as air is inhaled and exhaled during the respiratory cycle. Similarly, electromagnetic permeability of the body, and primarily of the trunk but the limbs also, changes with the cardiac cycle, presumably due to the fact that the volume and location of blood in the body varies with the cardiac cycle. Accordingly, it has been discovered in accordance with the present invention that it is possible to monitor the respiratory cycle, and the cardiac cycle as well, by directing an electromagnetic signal towards the body, and by detecting modulation of that signal in a receiver, the modulation being caused by varying permeability of the body during the respiratory and cardiac cycles. Preferred embodiments of a respiratory monitor (apnea detector) and optionally cardiac monitor which are constructed in accordance with the foregoing principles, are shown in the appended drawings.

The first preferred embodiment depicted in FIG. 1 includes a console 20, where electronic components (to be described below) are mounted. Additionally, a transmitter-transducer 22 is mounted in a suitable housing which is disposed in close proximity to the patient's body, and a receiver-transducer 24 in a suitable housing also disposed in close proximity to the patient's body at a location different than that of the transmitter-transducer 22. In the ensuing description the person or individual whose respiratory and cardiac cycles are monitored in accordance with the present invention, is referred to as the patient 26, mainly because a contemplated important use of the device of the invention is as an anti-respiration (apnea) monitor for individuals who suffer from various sleep disorders and respiratory diseases, and for infants to guard against "crib death" and sudden infant death syndrome (SIDS). Nevertheless, it should be understood that the monitoring device of the present invention may be used on individuals whose respiratory and cardiac cycle is to be monitored for reasons other than mentioned above, for example patients suffering, or suspected of suffering from diseases other than those mentioned above, and healthy individuals. The invention is therefore not limited by the purpose for which the invented monitor and process are used; in fact the invention can be used to monitor the respiratory and cardiac cycle of certain animals as well.

Figure 1:
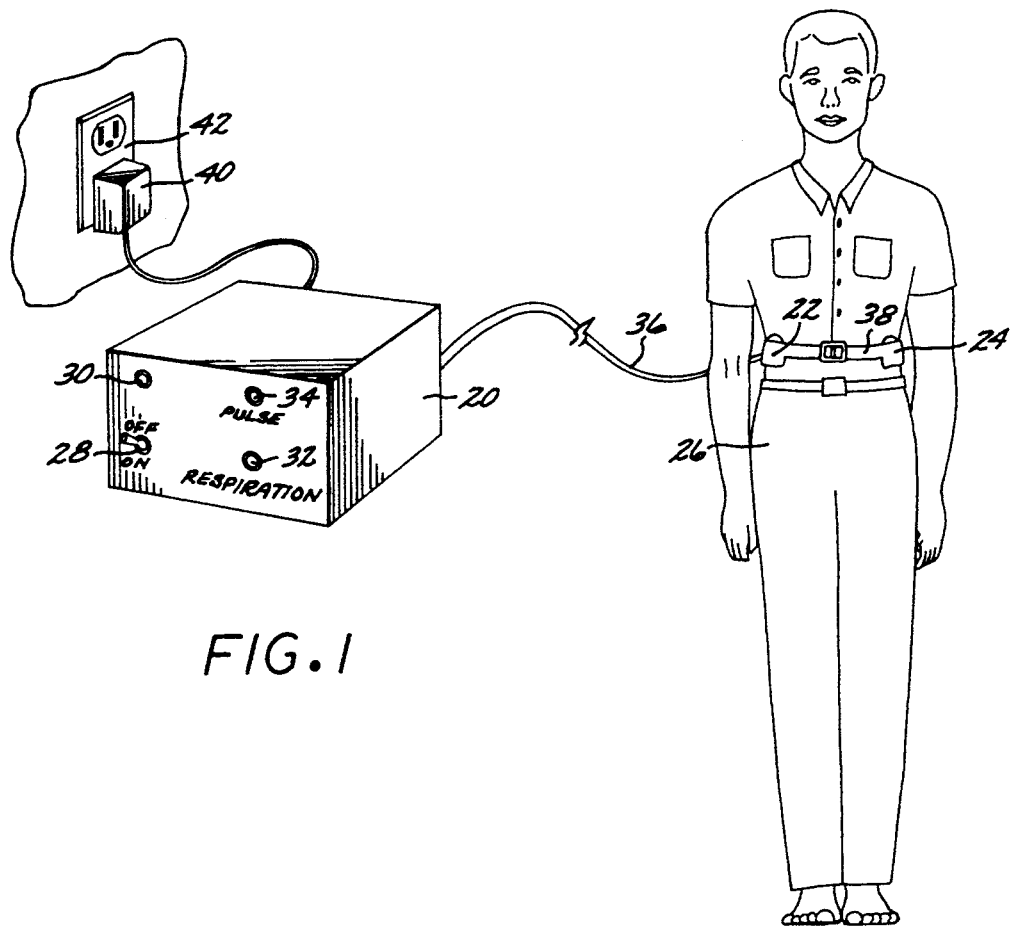
FIG. 1 is a schematic and perspective view showing the preferred embodiments of the respiratory and cardiac monitor (apnea detector) worn by a person.

Returning now to the description of FIG. 1, the console 20 of the first and second preferred embodiments includes an on-and-off switch 28, an indicator light 30 to show whether the system is powered to operate, and lights 32 and 34 to visually indicate the patient's respiration and pulse. A bundle of cables 36 connects the console with the transmitter-transducer 22 and receiver-transducer 24 which are conveniently mounted on a belt 38 worn by the patient 26. An important advantage of the present invention is that respiratory and cardiac monitoring is performed in a non-invasive manner. As is shown on the schematic view of FIG. 1, although the transmitter-transducer 22 and receiver-transducer 24 are located close to the body, they do not need to be in direct contact with the skin of the patient 26. The preferred embodiments shown in FIG. 1 receive their power from a transformer-rectifier 40 which is plugged into an ordinary 115 V AC wall outlet 42. As it is explained below in more detail in connection with FIG. 3, the respiratory monitor of the present invention can also be powered by rechargeable or non-rechargeable batteries.

Figure 2:
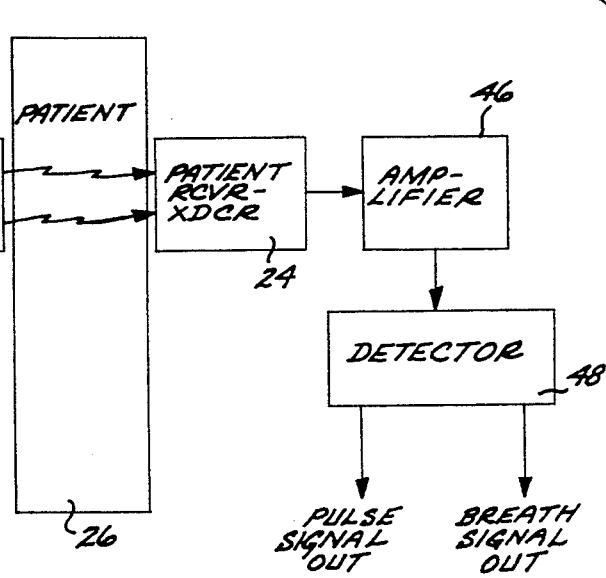
FIG. 2 is a block-diagrammatic representation of the circuitry of the first preferred embodiment.

Referring now to the block-diagrammatic view of FIG. 2, the main electronic components of the first preferred embodiment of the invention are shown. An oscillator circuit 44 (to be described in more detail in connection with FIG. 3) generates a symmetrical square wave signal of suitable frequency, which is amplified (the amplifier is shown on FIG. 3) and thereafter fed through the cables to the transmitter-transducer 22. In the transmitter-transducer 22 the square wave signal of the oscillator 44 is converted into a sinusoidal signal of substantially constant frequency and amplitude and is "transmitted", preferably by the use of a directional antenna to the patient's body.

The electromagnetic signal, which is modulated in its amplitude by the varying permeability of the patient's body, is received in the receiver-transducer 24, which preferably includes a directional antenna. The received signal is amplified in an amplifier 46 (preferably including several stages) and is fed into a detector circuit 48 which serves to separate the amplitude modulation caused by the varying permeability of the body from the constant carrier frequency generated in the transmitter-transducer 22. After the high frequency carrier signal is extinguished in the detector 48, the signal having modulation indicative of the patient's respiration and pulse is amplified further (the amplifiers are shown on FIG. 4) and is passed through high and low pass filters (shown on FIG. 4). In the herein described preferred embodiments the transmitter-transducer 22 transmits at a 100 KHz frequency, with an approximate possible range for operational frequency of the monitor being in the 20 KHz to 230 KHz range. After the high frequency of the carrier signal is extinguished in the detector circuit 48, the modulation corresponding to the respiratory cycle represents variation of less than approximately 3 cps, and is retained by the low pass filter having approximately the same cut-off point. Modulation corresponding to the patient's pulse represents variation in the signal of greater than approximately 4 cps frequency. This modulation is therefore retained by the high pass filter of approximately 4 cps cut-off. Accordingly, a respiratory signal and a pulse signal are obtained from the loss-pass and high pass filters respectively. The outputs are digital signals. These signals are used to control the respective lights 32 and 34 in the console 20, and may be utilized in various other manners, such as to be inputted into a computer (microprocessor) to be stored in memory, to trigger a warning signal, or the like.

Figure 3:
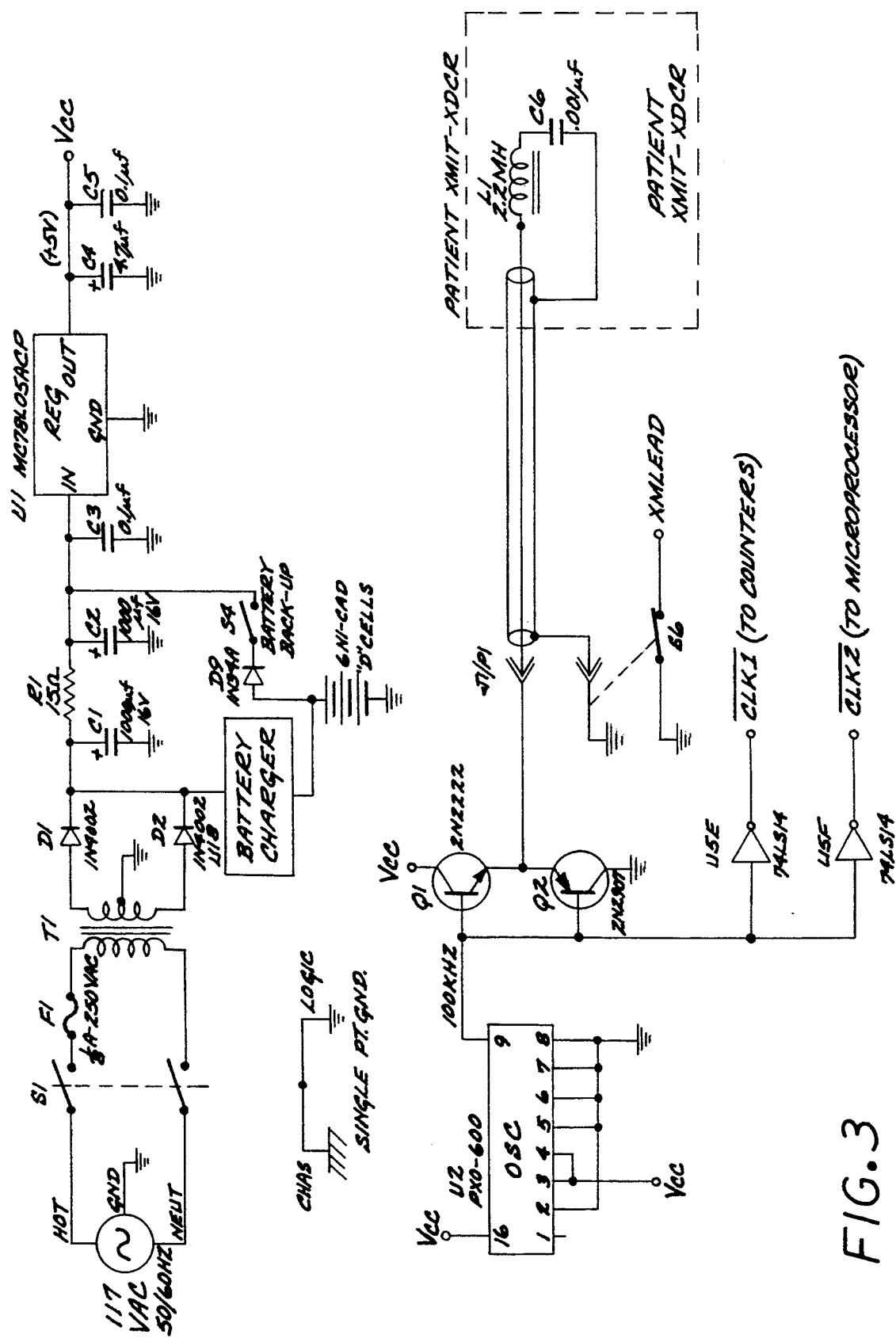
FIG. 3 is a circuit diagram showing the power supply, oscillator circuit and transmitter-transducer of the first and second preferred embodiments.
Figure 4:
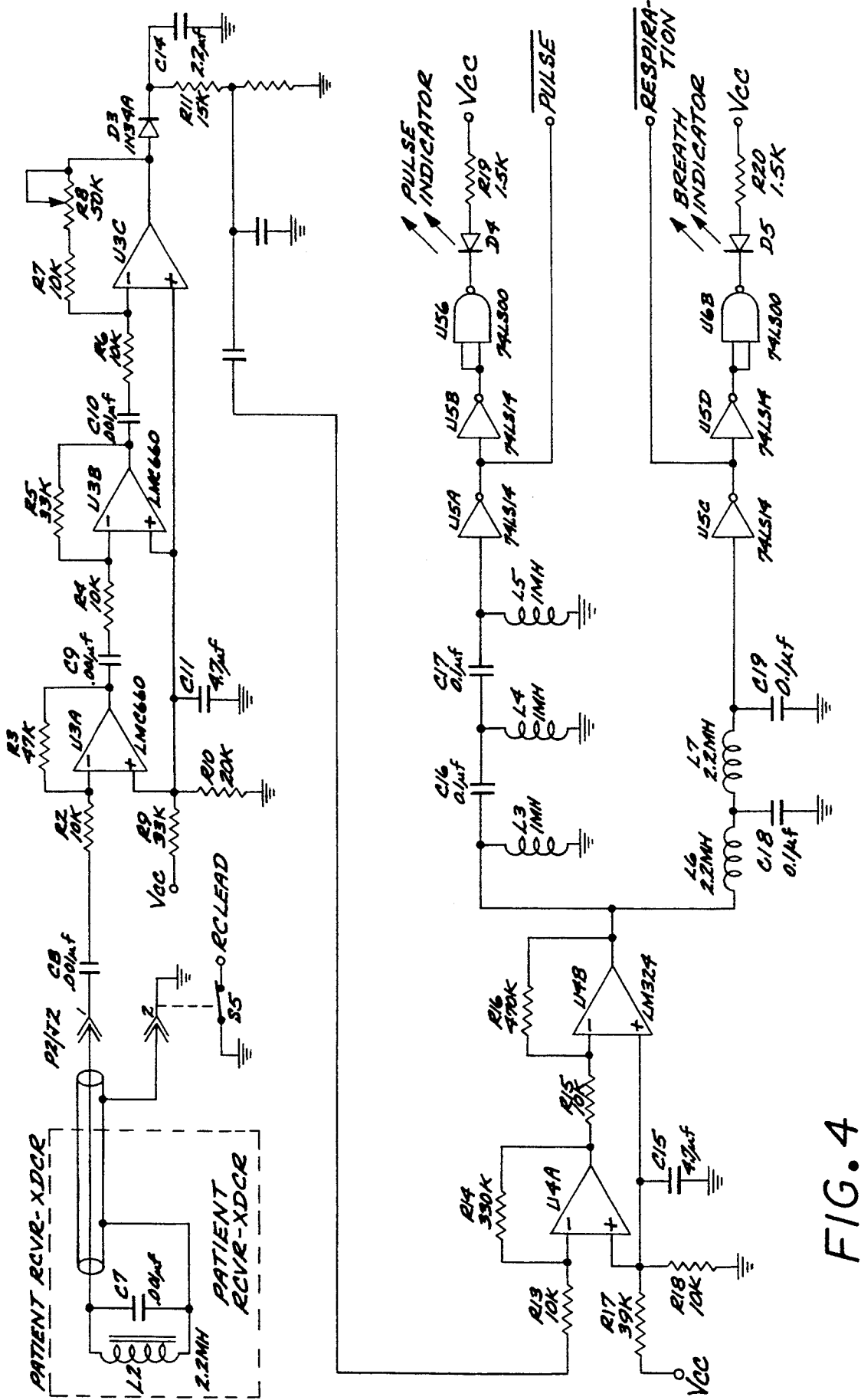
FIG. 4 is a circuit diagram showing the circuitry of a receiver transducer, amplifiers and detector filters and additional amplifiers of the first preferred embodiment.

Referring now to FIGS. 3 and 4 for a detailed description of the electronic components of the first preferred embodiment, the top portion of FIG. 3 shows the power supply. The power supply includes a battery back-up provision to provide the required voltages in the event of a power line failure. As can be seen, the power supply, T1, D1, D2, and C1, feed the battery charger module, U18, for recharging the rechargeable Ni-Cad batteries during the time when line power is present. Voltage regulator, U1, delivers a regulated +5 v for most circuit operations. Other voltages required are derived internally for the reference off-sets for the operational amplifiers.

Referring now to the lower part of FIG. 3 the transmitting portion of the monitor is shown. This includes the oscillator circuit 44 and the transmitter-transducer 22, and is used to include a constant amplitude magnetic signal to the patient. The transmitting portion has a switching oscillator, U2, operating at 100 KHz in this embodiment. The symmetrical square wave generated in the oscillator U2 is amplified by the push-pull emitter followers, Q1 and Q2. From the emitter follower Q2 the signal is fed to the transmitter-transducer 22. The transmitter-transducer 22 is a series resonant circuit comprised of L1 and C6, converting the square wave signal from the oscillator, U2, and the amplifiers, Q1 and Q2, into a sinusoidal magnetic waveform. An inductor, L1, is housed in a ferrite material cup-shaped magnetic core providing a very high "Q" circuit and a directional antenna inducing this constant amplitude magnetic signal into the patient's body.

Referring now to FIG. 4 the receiving portion of the monitor of the first preferred embodiment is shown. The receiving portion is used to detect the modulated signal resulting from the changing electromagnetic permeability in the body tissues. A component of the receiving portion is the receiver-transducer 24. This is a parallel resonant circuit comprised of L2 and C7. An inductor, L2, is housed in a ferrite material cup-shaped core also provides a very high "Q" circuit and a directional antenna for the receiver-transducer 24. The received signal has been modulated by the change in the electromagnetic permeability of the body tissues during the cycles of respiration and cardiac activity. The received signal is amplified by the amplifiers, U3A, U3B, and U3C, and fed to the diode detector, D3, C14, R11, R12, and C13. At this point, the high frequency magnetic signal is extinguished, and remaining modulation of both respiration and pulse are fed through the coupling capacitor, C12, to amplifiers U4A and U4B. The output of amplifier U4B is fed into parallel filters for separation of the signals of pulse and respiration. The low-pass filter, L6, L7, C18, and C19, extinguishes the pulse signal, and feeds the respiration signal to schmitt trigger, U5C, for digitizing, further processing, and indicating. The high-pass filter, L3, L4, L5, C16, and C17, extinguishes the respiration signal, and the pulse signal is fed into schmitt trigger, U5A, for digitizing, further processing, and indicating.

Figure 5:
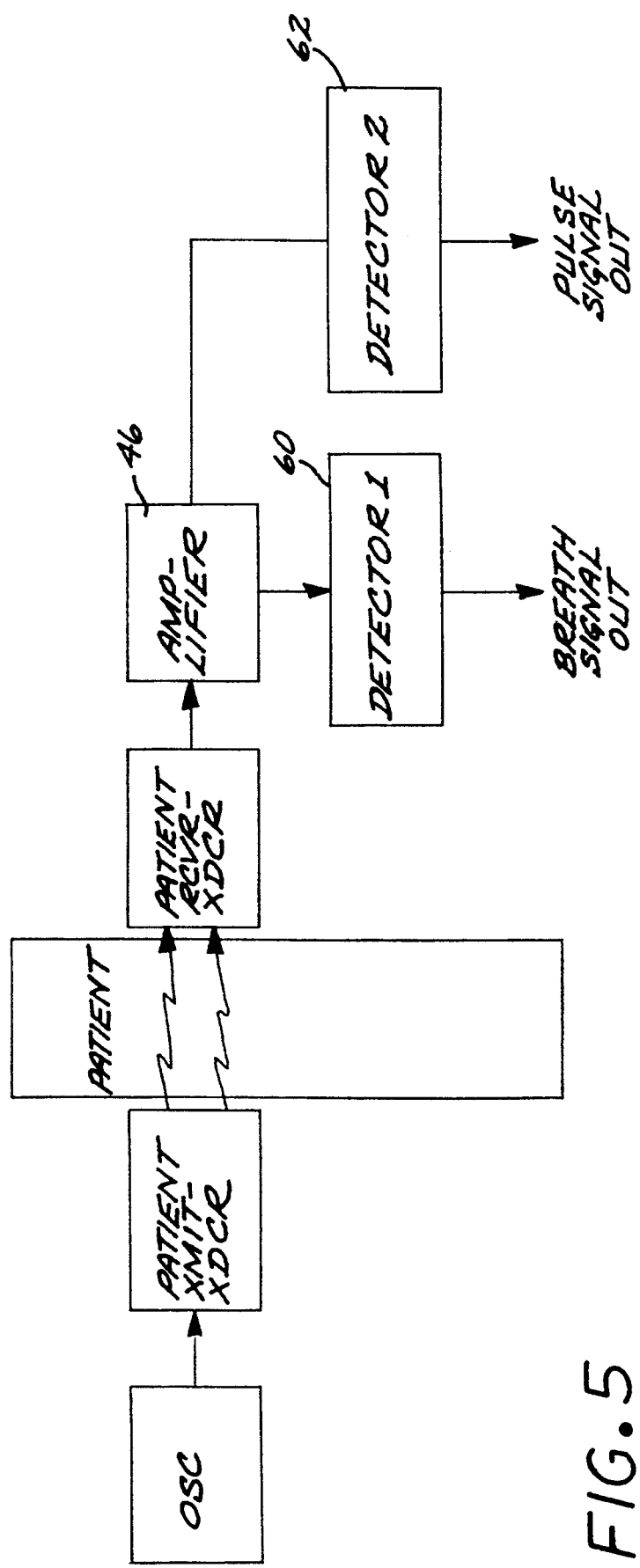
FIG. 5 is a block-diagrammatic representation of the circuitry of the second preferred embodiment.

FIG. 5 is block diagrammatic representation of the main electronic components of the second preferred embodiment of the present invention. These are identical or substantially identical with the electronic components of the first preferred embodiments, except that in the second preferred embodiment processing of the signal received by the receiver transducer is electronically different than in the first preferred embodiment. Thus, still with particular reference to FIG. 5, the signal received in the receiver-transducer is amplified in the amplifier 46 (preferably in several stages) and is thereafter inputted into two separate detectors, indicated on the block-diagram of FIG. 5 as "DETECTOR 1" and "DETECTOR 2", which are, respectively, detectors for the respiratory signal 60, and detectors for the pulse signal 62. The output of each of these detectors 60 and 62 is the respiratory signal and the pulse signal, respectively.

Figure 6:
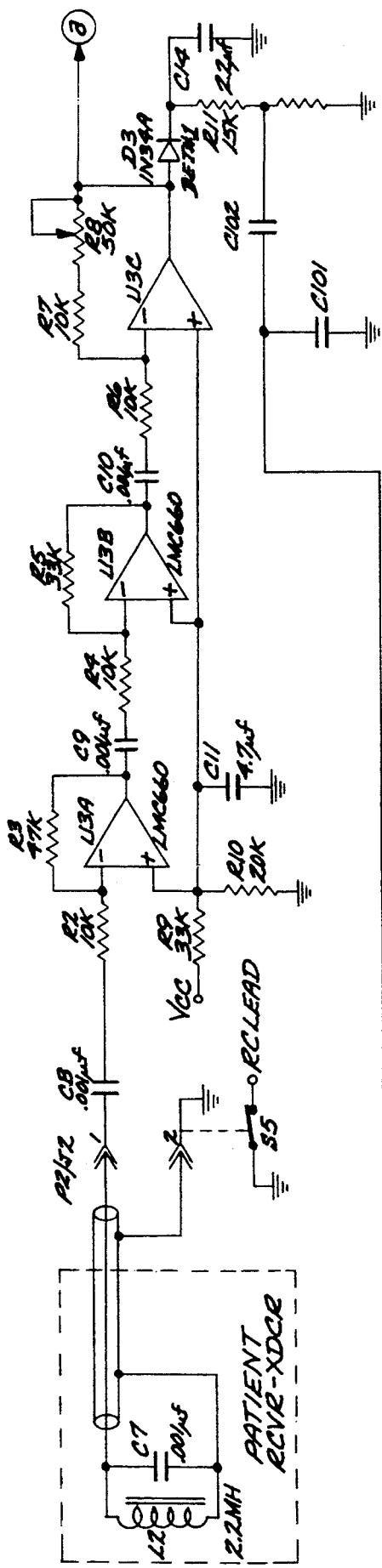
FIG. 6 is a circuit diagram showing the circuitry of a receiver transducer, amplifiers and detector of the respiratory signal of the second preferred embodiment.
Figure 6:
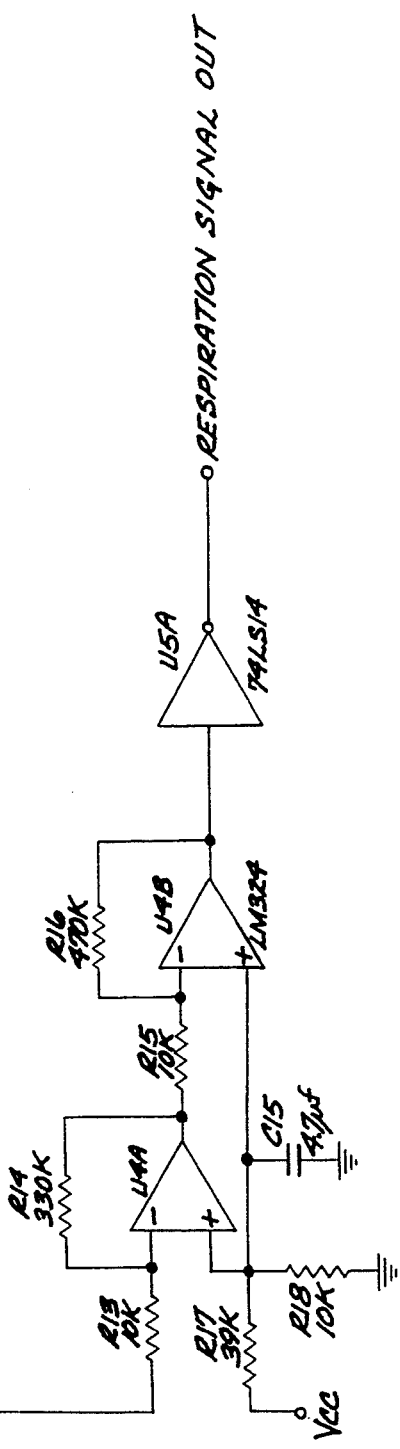

FIG. 6 illustrates in detail a portion of the receiving circuit and the detector circuit for the respiratory signal of the second preferred embodiment. The part of this circuit which is illustrated on the top portion of this drawing figure is identical with the corresponding part of the circuit of the first preferred embodiment, as is shown on the top portion of FIG. 4. Thus, the amplified signal (output of operational amplifiers U3A, U3B and U3C) is split, in the sense that it is inputted into two separate detector circuits. The detector circuit for the respiratory signal includes the diode D3 (also present in the circuit shown on FIG. 4) where the oscillator frequency is extinguished. From diode D3 the signal is passed through capacitors C101 and C102, which act as low pass filters having a cut-off of approximately 3 cps. From this low pass filter the signal is inputted into amplifiers U4A and U4B and from there into schmitt trigger digital amplifier U5A. The operational amplifiers U4A and U4B and the schmitt trigger U5A are shown in the lower portion of FIG. 6. The output of schmitt trigger U5A is the respiratory signal.

Figure 7:
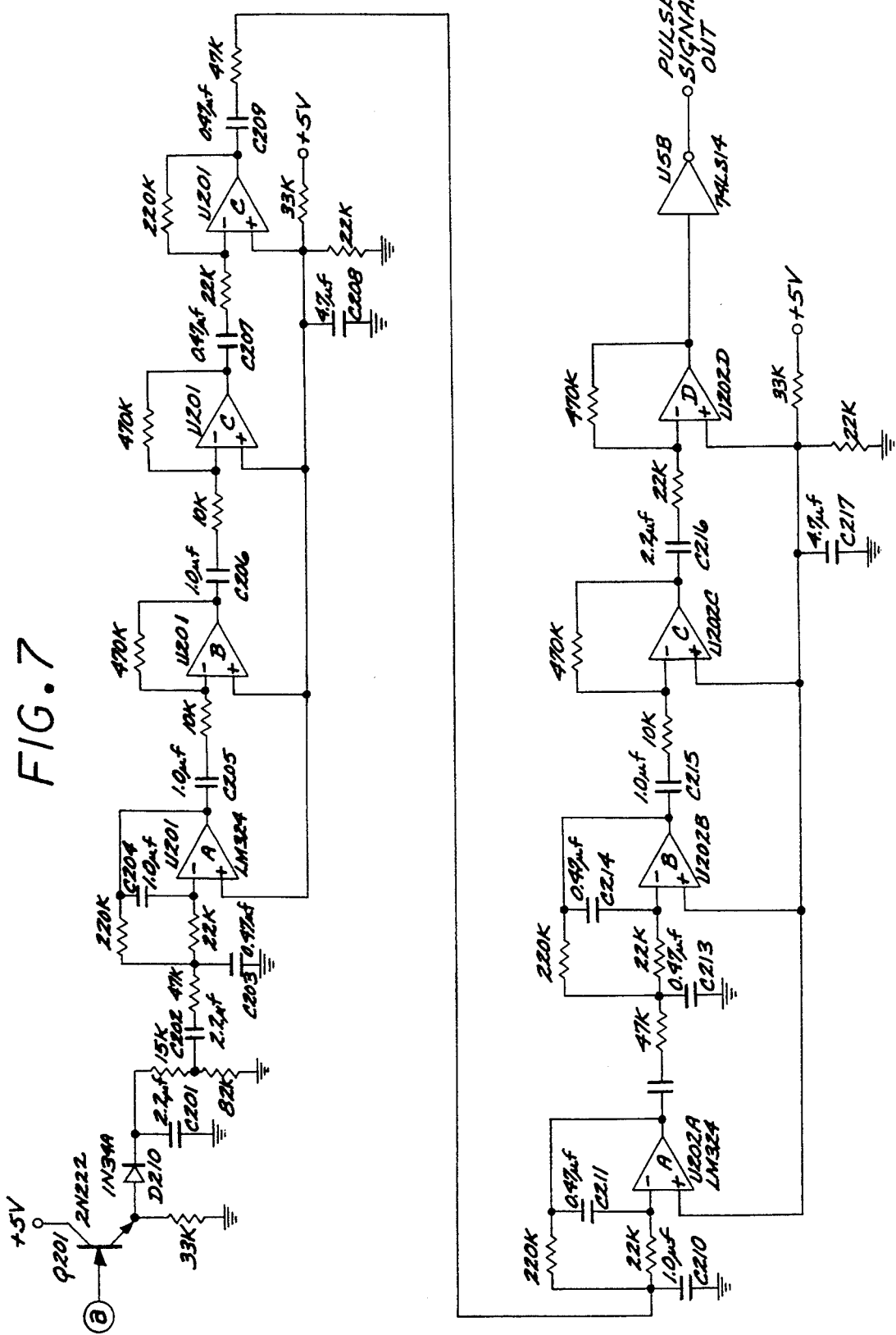
FIG. 7 is a circuit diagram showing the circuitry of the detector active filters and additional amplifiers of the cardiac signal of the second preferred embodiment.

FIG. 7 illustrates the details of the detector 62 for the pulse cycle. The input of this detector circuit is the output of operational amplifier U3C shown on FIG. 6. Thus, as is shown on FIG. 7, the signal proceeds through emitter follower Q201, through diode D210, then through high pass filter which includes capacitor C202. The cut-off of the high pass filter is approximately 3 cps. From the high pass filter the signal is inputted into active filter which includes operational amplifier U201A. In the active filter there is a gain of the pulse signal, and the filter cuts off frequencies above approximately 20 cps. It was found in accordance with the present invention that the use of a filter to cut off spurious frequencies above 20 cps is highly desirable to eliminate or minimize interference by the virtually ubiquitous 60 cps household current signal. After the active filter the signal is processed through amplifiers U201B, U201C and U201D. The output of operational amplifier U201D is processed through more stages of active filtering in devices U202A and U202B. These active filters also have a cut off frequency of approximately 20 cps, and they serve to further eliminate any spurious signals which may have leaked through. The output of the last active filter U202B is amplified further in operational amplifiers U202C and U202D. The signal is thereafter digitized in schmitt trigger U5B, and the output of this schmitt trigger is the pulse signal.

It is believed that a person having ordinary skill in the electronic arts can readily construct the monitor of the invention from commercially available electronic components, based on the foregoing description and the appended drawing figures.

Several modifications of the present invention may also become readily apparent to those skilled in the art in light of the foregoing disclosure. One readily apparent modification is an embodiment wherein only the cardiac cycle is monitored. Because, the magnetic permability of the limbs of the body also varies with the cardiac cycle (as noted above), a cardiac cycle monitor can be designed in such a manner in accordance with the principles of the present invention that the trasmitter and receiver of the electromagnetic signals are mounted to the limbs (for example an arm) rather than to the trunk of the body. In light of the foregoing, the scope of the present invention should be interpreted solely from the following claims, as such claims are read in light of the disclosure.

What is claimed is:

1. A respiratory monitor for a human patient, the monitor comprising:
   first transmitter means adapted to be placed in close proximity of the body of the patient for transmitting an electromagnetic carrier signal in the direction of the patient's body;
   transducer means adapted to be placed in close proximity of the body of the patient for receiving the electromagnetic signal transmitted by the transmitter, the transducer means being in a location such that the electromagnetic signal of the transmitter means is transmitted to the transducer through the patient's body, the electromagnetic signal being modulated by the varying permeability of the patient's body caused by the patient's respiration, an output of the transducer means reflecting said modulated electromagnetic signal, and
   signal decoding means operatively connected to the transducer means and receiving the output of the transducer means, for decoding the modulated electromagnetic signal and for producing a second signal which is indicative of the varying permeability of the patient's body and is therefore indicative of the patient's respiration.

2. The monitor of claim 1 further comprising oscillator means operatively connected to the transmitter means for generating the electromagnetic signal transmitted by the transmitter means.

3. The monitor of claim 1 wherein the transmitter means transmits a carrier signal of substantially constant frequency.

4. The monitor of claim 3 wherein the transmitter means transmits a sinusoidal carrier signal of substantially constant frequency.

5. The monitor of claim 3 wherein the signal decoding means include detector means operatively connected to the transducer means for receiving output of the transducer means and for separating the substantially constant frequency of the carrier signal from modulation which is indicative of the patient's respiration, and for generating an amplitude modulated second signal indicative of said respiration.

6. The monitor of claim 5 wherein the signal decoding means further include first amplifier means for amplifying the signal outputted by the transducer means.

7. The monitor of claim 6 wherein the signal decoding means further comprise second amplifier means for amplifying the signal outputted by the detector means.

8. The monitor of claim 5 wherein the transducer means comprises a parallel resonance tuned circuit.

9. The monitor of claim 1 wherein the transmitter means and the transducer means are mounted on a garment worn by the patient.

10. The monitor of claim 1 further comprising display means for displaying a visual symbol indicative of the respiration of the patient, the display means receiving as input the second signal from-the signal decoding means.

11. The monitor of claim 10 further comprising warning means for activating an alarm when the second signal received in the warning means from the signal decoding means indicates absence of respiration for the duration of a predetermined period of time.

12. A respiratory and cardiac monitor for a human patient, the monitor comprising:
    transmitter means adapted to be placed in close proximity of the body of the patient for transmitting an electromagnetic carrier signal at least in the direction of the patient's body;
    transducer means adapted to be placed in close proximity of the body of the patient for receiving the electromagnetic signal transmitted by the transmitter, the transducer means being in a location such that the electromagnetic signal of the transmitter means is transmitted to the transducer through the patient's body, the electromagnetic signal being modulated by the varying electromagnetic permeability of the patient's body reflecting respiration and cardiac activity of the patient, the transducer means outputting a second signal which is indicative of the modulated signal received by the transducer means;
    signal decoding means connected to the transducer means for receiving the output of the transducer means and for decoding the second signal and for producing a third signal which is indicative of the patient's respiration and a fourth signal which is indicative of the patient's cardiac activity, and
    oscillator means operatively connected to the transmitter means for generating the electromagnetic signal transmitted by the transmitter means.

13. The monitor device of claim 12 wherein the transmitter means transmits a carrier signal of substantially constant frequency.

14. The monitor of claim 13 wherein the transmitter means transmits a sinusoidal carrier signal of substantially constant frequency.

15. The monitor of claim 14 wherein the signal decoding means include detector means for receiving the output of the transducer means and for separating the substantially constant frequency of the carrier signal from modulation which is indicative of the patient's respiration and cardiac activity, and for generating the amplitude modulated third signal indicative of said respiration and the amplitude modulated fourth signal indicative of said cardiac activity.

16. The monitoring device of claim 15 wherein the signal decoding means further include low pass filter means for outputting a signal having a modulation of a frequency lower than approximately 3 cps, said outputted signal lower than approximately 3 cps frequency being the third signal indicative of the respiration of the patient, and where the signal decoding means still further include high pass filter means for outputting a signal having a modulation of a frequency higher than approximately 4 cps, said outputted signal of higher than approximately 4 cps frequency being the fourth signal indicative of the cardiac activity of the patient.

17. The monitor of claim 16 further comprising first display means for displaying a first visual symbol indicative of the respiration of the patient, the first display means receiving as input the output of the low pass filter means, and a second display means for displaying a second visual symbol indicative of the cardiac activity of the patient, the second display means receiving as input the output of the high pass filter means.

18. The monitor of claim 15 wherein the signal decoding means further include first amplifier means for amplifying the second signal outputted by the transducer means.

19. The monitor of claim 18 wherein the signal decoding means include filter means having a cut off of approximately 20 cps for eliminating spurious signal components in said third and fourth signals.

20. The monitor of claim 13 wherein the transducer means comprises a parallel resonance tuned circuit.

21. The monitor of claim 12 wherein the transmitter means and the transducer means are mounted on a garment to be worn by the patient.

22. The monitor of claim 21 wherein the oscillator means and the signal decoding means are mounted in a console which is connected to the transmitter means and transducer means by cables.

23. A respiratory and cardiac monitor for a human patient, the monitor comprising:
    oscillator means powered by a direct current voltage for generating as its output a square wave signal of substantially constant frequency;
    first amplifier means for receiving the output of the oscillator means and for generating an amplified square wave signal as its output;
    transmitter means adapted to be placed in close proximity of the body of the patient for receiving the output of the first amplifier means and for generating as its output a sinusoidal electromagnetic signal of substantially constant amplitude and substantially of the same constant frequency as the square wave generated in the oscillator means, the outputted electromagnetic signal of the transmitter means being directed towards the patient's body;
    receiver-transducer means adapted to be placed in close proximity of the body of the patient for receiving the electromagnetic signal transmitted by the transmitter, the receiver-transducer means being in a location such that the electromagnetic signal of the transmitter means is transmitted to the receiver-transducer through the patient's body, the electromagnetic signal being modulated by the varying electromagnetic permeability of the patient's body reflecting respiration and cardiac activity of the patient, the receiver-transducer means outputting an amplitude modulated second signal which is indicative of the signal received by the receiver-transducer means;

second amplifier means for receiving the output of the receiver-transducer means and for producing as its output an amplified amplitude modulated signal which is indicative of the signal received by the receiver-transducer means;

detector means for receiving the output of the second amplifier means and for extinguishing the frequency corresponding to the sinusoidal signal generated by the transmitter means and for generating as its output an amplitude modulated signal indicative of the varying permeability of the patient's body caused by respiration and cardiac activity;

third amplifier means for receiving the output of the detector means and for generating as its output an amplified amplitude modulated signal indicative of the varying permeability of the patient's body caused by respiration and cardiac activity;

low pass filter means for receiving the output of the third amplifier means and for outputting a signal having a modulation of a frequency lower than approximately 3 cps, said outputted signal lower than approximately 3 cps frequency being indicative of the respiration of the patient;

high pass filter means for receiving the output of the third amplifier means and for outputting a signal having a modulation of a frequency higher than approximately 4 cps, said outputted signal of higher than approximately 4 cps frequency being indicative of the cardiac activity of the patient;

first display means for displaying a first visual symbol indicative of the respiration of the patient, the first display means receiving as input the output of the low pass filter means, and a second display means for displaying a second visual symbol indicative of the cardiac activity of the patient, the second display means receiving as input the output of the high pass filter means.

24. The monitor of claim 23 wherein the first amplifier means comprise a push-pull emitter follower amplifier.

25. The monitor of claim 24 wherein the receiver-transducer means comprise a parallel resonance tuned circuit.

26. The monitor of claim 23 further comprising analog to digital converter means for converting into respective digital signals the respective outputs of the low pass and of the high pass filter means.

27. The monitor of claim 23 where the transmitter means and the receiver-transducer means are mounted on a garment to be worn by the patient.

28. A method for monitoring the respiration of a human, the method comprising:

transmitting from a source disposed in close proximity to the human's body an electromagnetic carrier signal having a carrier frequency, in the direction of the human's body;

receiving the signal in a receiver-transducer disposed in close proximity to the human's body, the signal being modulated by varying electromagnetic permeability of the body which is affected by respiration and cardiac activity of the human;

demodulating the signal received in the receiver to separate the carrier frequency and to output a modulated signal indicative of the respiration and cardiac activity of the human, and displaying an audio-visual signal derived from said modulated signal and indicative of the respiration of the human.

29. The method of claim 28 wherein the step of transmitting comprises a step of transmitting a sinusoidal carrier signal of substantially constant frequency.

30. The method of claim 28 further comprising the steps of separating the modulated signal into components indicative of the respiration and cardiac activity of the human, and displaying a second audio-visual signal derived from the component of the modulated signal which is indicative of the respiration of the human.

31. A cardiac monitor for a human patient, the monitor comprising:

first transmitter means placed in close proximity of the body of the patient for transmitting an electromagnetic carrier signal in the direction of the patient's body;

transducer means adapted to be placed in close proximity of the body of the patient for receiving the electromagnetic signal transmitted by the transmitter, the transducer means being in a location such that the electromagnetic signal of the transmitter means is transmitted to the transducer through the patient's body, the electromagnetic signal being modulated by the varying permeability of the patient's body caused by the patient's cardiac cycle, an output of the transducer means reflecting said modulated electromagnetic signal, and signal decoding means operatively connected to the transducer means and receiving the output of the transducer means, for decoding the modulated electromagnetic signal and for producing a second signal which is indicative of the varying permeability of the patient's body and is therefore indicative of the patient's cardiac cycle.

32. The monitor of claim 31 further comprising oscillator means operatively connected to the transmitter means for generating the electromagnetic signal transmitted by the transmitter means.

33. The monitor of claim 31 wherein the transmitter means transmits a carrier signal of substantially constant frequency.

34. The monitor of claim 33 wherein the transmitter means transmits a sinusoidal carrier signal of substantially constant frequency.

35. The monitor of claim 33 wherein the signal decoding means include detector means operatively connected to the transducer means for receiving output of the transducer means and for separating the substantially constant frequency of the carrier signal from modulation which is indicative of the patient's cardiac cycle, and for generating an amplitude modulated second signal indicative of said cardiac cycle.

36. The monitor of claim 35 wherein the signal decoding means further include first amplifier means for amplifying the signal outputted by the transducer means.

37. The monitor of claim 36 wherein the signal decoding means further comprise second amplifier means for amplifying the signal outputted by the detector means.

38. The monitor of claim 35 wherein the transducer means comprises a parallel resonance tuned circuit.

39. The monitor of claim 31 wherein the transmitter means and the transducer means are adapted to be mounted to a limb of the patient.

40. The monitor of claim 31 further comprising display means for displaying a visual symbol indicative of the cardiac cycle of the patient, the display means receiving as input the second signal from the signal decoding means.

* * * * *